US012796908B2

(12) United States Patent
Kalamkar et al.

(10) Patent No.: US 12,796,908 B2
(45) Date of Patent: Nov. 17, 2026

(54) DETECTING A VISUAL INDICATOR OF AN OCCLUDER FOR AN EYE EXAMINATION

(71) Applicant: Verily Health Inc., Dallas, TX (US)

(72) Inventors: Abhijit Kalamkar, Sunnyvale, CA (US); Supriyo Sinha, Menlo Park, CA (US); Jeremy Chan, San Jose, CA (US); Dimitri Azar, Chicago, IL (US)

(73) Assignee: Verily Health Inc., Dallas, TX (US)

( * ) Notice: Subject to any disclaimer, the term of this patent is extended or adjusted under 35 U.S.C. 154(b) by 229 days.

(21) Appl. No.: 18/631,896

(22) Filed: Apr. 10, 2024

(65) Prior Publication Data

US 2025/0072743 A1 Mar. 6, 2025

Related U.S. Application Data

(60) Provisional application No. 63/579,441, filed on Aug. 29, 2023.

(51) Int. Cl.
*A61B 3/00* (2006.01)

(52) U.S. Cl.
CPC .......... *A61B 3/0066* (2013.01); *A61B 3/0041* (2013.01)

(58) Field of Classification Search
CPC ............................ A61B 3/0066; A61B 3/0041
USPC .......................................................... 351/200
See application file for complete search history.

(56) References Cited

U.S. PATENT DOCUMENTS 5,191,897 A 3/1993 Meshel et al.
5,946,075 A * 8/1999 Horn ...................... A61B 3/022 351/237
6,179,421 B1 1/2001 Pang
7,926,943 B1 * 4/2011 Reichow .............. A61B 3/0033 351/203
7,976,162 B2 7/2011 Flitcroft
10,470,654 B2 11/2019 Schmid et al.
11,432,718 B2 9/2022 Xu et al.
(Continued)

FOREIGN PATENT DOCUMENTS

CN 109464118 A 3/2019
WO 2020176784 A1 3/2020

OTHER PUBLICATIONS

Korean Intellectual Property Office, International Search Report and Written Opinion for PCT/US2024/043108, Dec. 4, 2024, 7 pages.

*Primary Examiner* — Sharrief I Broome
(74) *Attorney, Agent, or Firm* — Christensen O'Connor Johnson Kindness PLLC

(57) ABSTRACT

Systems, devices, and methods for detecting a visual indicator of an occluder for an eye examination are provided. In one example, a device may be used to administer an eye examination by detecting, via a camera of the device, a visual indicator located on an occluder while the occluder is covering at least a portion of a user's face. The device can configure a graphical user interface to display, at a display screen of the device, an eye examination administered to the user. The device can output, via the display screen, a result of the eye examination based on information encoded by the visual indicator. In some implementations, the detecting may include detecting an opaque surface of the occluder covering an eye of the user. In some implementations, the detecting may include detecting a lens of the occluder covering an eye of the user.

21 Claims, 5 Drawing Sheets

(56) References Cited

U.S. PATENT DOCUMENTS

| | | | | |
|---|---|---|---|---|
| 2013/0128229 | A1* | 5/2013 | Huang | A61B 3/028 351/239 |
| 2016/0184170 | A1 | 6/2016 | Bunker | |
| 2017/0127942 | A1* | 5/2017 | Sakurada | A61B 3/18 |
| 2018/0103841 | A1 | 4/2018 | Sprowl | |
| 2019/0012784 | A1 | 1/2019 | Wiley | |
| 2019/0046029 | A1 | 2/2019 | Tomasi et al. | |
| 2019/0082951 | A1 | 3/2019 | Merriam et al. | |
| 2019/0110679 | A1 | 4/2019 | Mackool et al. | |
| 2019/0133437 | A1 | 5/2019 | Sugawara et al. | |
| 2020/0069173 | A1 | 3/2020 | Jensen et al. | |
| 2020/0178792 | A1 | 6/2020 | Mackool et al. | |
| 2020/0285062 | A1 | 9/2020 | Grutman et al. | |
| 2022/0117695 | A1 | 4/2022 | Weissman et al. | |
| 2022/0133212 | A1 | 5/2022 | Krueger | |
| 2023/0004008 | A1 | 1/2023 | Samec et al. | |
| 2023/0036308 | A1* | 2/2023 | Lee | A61B 3/0041 |
| 2023/0255473 | A1* | 8/2023 | Srinivasan | A61B 3/028 351/222 |
| 2025/0204771 | A1 | 6/2025 | Chan et al. | |

* cited by examiner

DETECTING A VISUAL INDICATOR OF AN OCCLUDER FOR AN EYE EXAMINATION

CROSS-REFERENCE AND RELATED APPLICATIONS

This patent application claims priority to U.S. Provisional Application No. 63/579,441, filed Aug. 29, 2023, which is hereby incorporated by reference in its entirety.

FIELD

This disclosure relates generally to utilizing a computing device for an eye examination and, more specifically, to detecting a visual indicator of an occluder for an eye examination. Other aspects are also described.

BACKGROUND

An occluder is a structure that may be used during the administration of an eye examination (e.g., an eye test, such as a test for visual acuity). An occluder can be configured to block all light (e.g., a complete occluder) or a portion of light (e.g., a pinhole occluder) to an eye of a patient. Blocking the light can enable one or more eye examinations to be performed.

SUMMARY

Implementations of this disclosure include configuring an occluder with a visual indicator that a device can detect and use to configure an eye examination administered to a user. In some cases, the occluder and the device may be used in a system to perform a self-administered eye examination. Some implementations may include a device that detects, via a camera, a visual indicator located on an occluder while the occluder is covering at least a portion of a user's face. The device may configure a graphical user interface (GUI) to display at a display screen of the device an eye examination administered to the user. The device may then output a result of the eye examination based on information encoded by the visual indicator. In some implementations, the detecting may include detecting an opaque surface of the occluder covering an eye of the user. In some implementations, the detecting may include detecting a lens of the occluder covering an eye of the user. Other aspects are also described and claimed.

The above summary does not include an exhaustive list of all aspects of the present disclosure. It is contemplated that the disclosure includes all systems and methods that can be practiced from all suitable combinations of the various aspects summarized above, as well as those disclosed in the Detailed Description below and particularly pointed out in the Claims section. Such combinations may have particular advantages not specifically recited in the above summary.

BRIEF DESCRIPTION OF THE DRAWINGS

Several aspects of the disclosure here are illustrated by way of example and not by way of limitation in the figures of the accompanying drawings in which like references indicate similar elements. It should be noted that references to "an" or "one" aspect in this disclosure are not necessarily to the same aspect, and they mean at least one. Also, in the interest of conciseness and reducing the total number of figures, a given figure may be used to illustrate the features of more than one aspect of the disclosure, and not all elements in the figure may be required for a given aspect.

DETAILED DESCRIPTION

Figure 1:
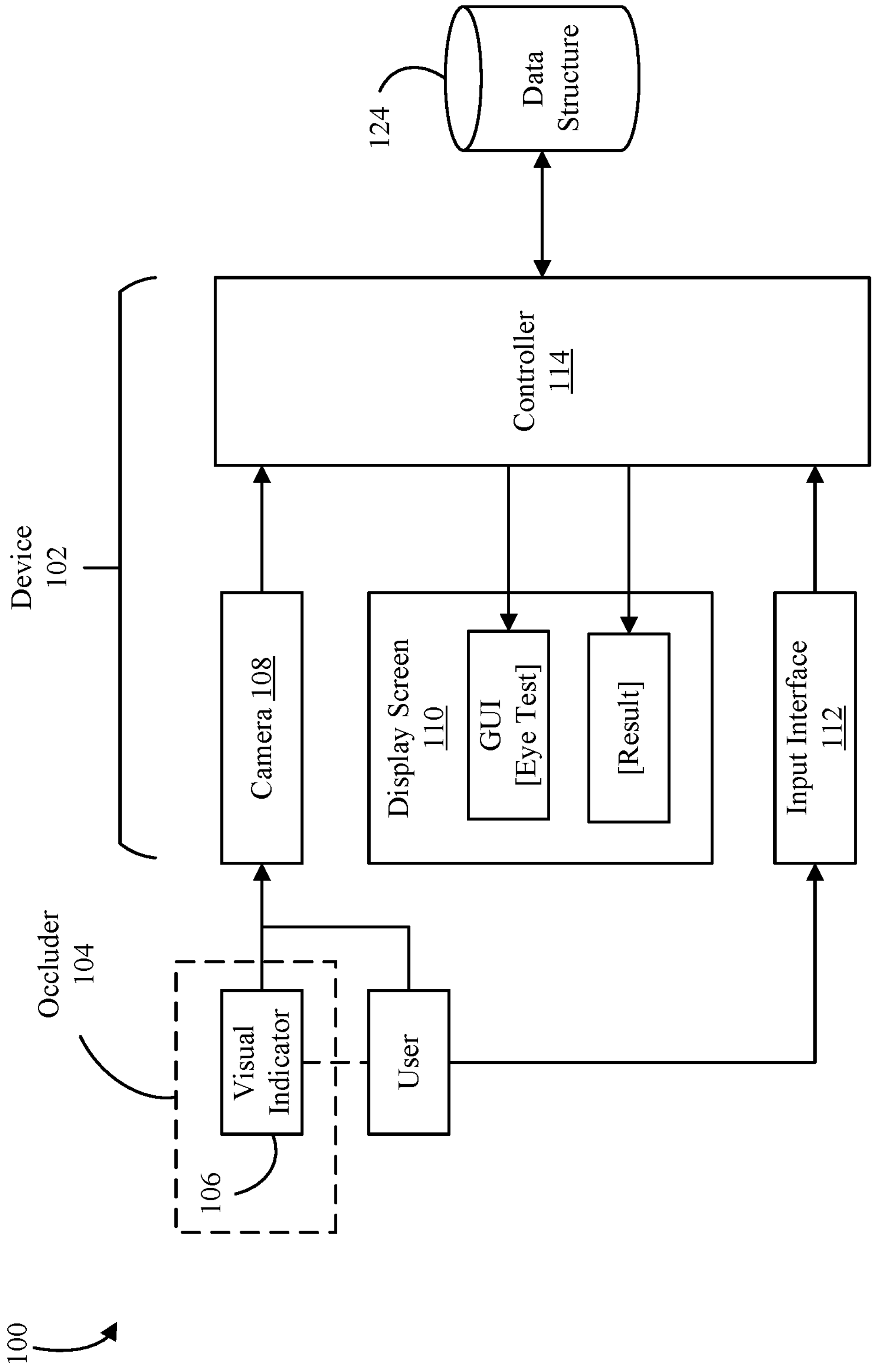
FIG. 1 is a block diagram of an example of system for detecting a visual indicator of an occluder for an eye examination.

A user can utilize a computing device, such as handheld computer running a program or application (e.g., a smartphone or tablet computer), to self-administer an eye examination. For example, the eye examination could be an eye test for visual acuity, astigmatism, or color blindness. In some cases, the eye examination may require that one of the user's eyes remains open while the other of the user's eyes is closed. However, the user might close the wrong eye for the test administered by the application or might not close their eye at all. Additionally, based on the closeness of the device's display screen to the user's face (e.g., a smartphone or tablet computer held at arm's length), the application might not obtain accurate results. For example, the eye examination administered by the application to the display screen might not be properly configured in size for the relatively close distance of the user to the display screen.

To improve results when administering an eye examination, an occluder can be used by the user. The occluder can include an opaque surface that blocks all light (e.g., a complete occluder) to one of the user's eyes (e.g., the untested eye), and could either transmit all light (e.g., no occlusion) or transmit a portion of light (e.g., a pinhole occluder) to the other of the user's eyes (e.g., the tested eye). This can help the user to ensure that the correct eye is closed when performing the eye test. Additionally, the occluder can include a lens over the other of the user's eyes to simulate distance vision between the user and the display screen of the device. The lens can be configured in the occluder with different powers to simulate different distances between the user's face and the display screen. This can be used to simulate a correct distance when performing the eye test (e.g., 20 feet).

The application running on the device can then receive information about the occluder from the user. For example, the user can input information to confirm that a certain occluder is being used to cover one of the user's eyes, and/or that the occluder includes a certain power of lens over the other of the user's eyes to simulate distance vision. However, requiring the user to input this information can cause inconvenience to the user and possibly errors in the eye examination, such as by the user incorrectly entering the power of lens being used. Further, requiring the user to input this information can cause delays in the performance of the eye examination (e.g., the application waiting for the input from the user).

Implementations of this disclosure address problems such as these by configuring an occluder (e.g., used by a subject, such as a user of a device) with a visual indicator that a device can detect and use to configure an eye examination (e.g., a visual acuity test). In some cases, the occluder and the device may be used in a system to perform a self-administered eye examination by a user of the device. Some implementations may include a device such as a handheld computer (e.g., a smartphone or tablet). The device may detect, via a front facing built-in camera of the device, a visual indicator located on an occluder while the occluder is covering at least a portion of the user's face. The device may configure a GUI to display at a front facing built-in display screen of the device (e.g., a touchscreen) an eye examination administered to the user (e.g., a Snellen chart when testing visual acuity). The device may then output a result of the eye examination (e.g., a confirmation or score of the eye examination, output to the display screen or to speakers or headphones of the device) based on test input from the user and information encoded by the visual indicator. As a result, an eye examination can be administered to a user while reducing inconvenience to the user, errors in the eye examination, and/or delays in the performance of the eye examination.

In some implementations, the device running the application may be configured to perform a self-administered eye test. The device could be a smartphone or a tablet with front facing camera and display screen oriented in the same direction. The device may (1) detect that a subject (e.g., the user) is at required distance, (2) detect that the subject has covered their eye (e.g., the left eye or the right eye) for the required test, and (3) identify an occluder the subject is using to cover the eye. The occluder may include the visual indicator (e.g., a symbol) to enable identifying the occluder from an encoding of a description about the occluder. For example, the description may include an identification number, indication of a lens fitted on the occluder, indication of a power of the lens, information about the user, and/or indication of a type of the occluder for which eye tests may be performed (e.g. utilized for distance vision simulation). In some implementations, the application running on the device can automatically recognize the details of the occluder (e.g., the information) without the subject entering the information manually, thereby reducing inconvenience, errors, and/or delays.

In some implementations, the occluder may comprise a simple structure, such as a piece of paper, cardboard, or plastic, with a quick response (QR) code or other visual symbol located on the structure. In some cases, the occluder might not include a lens (e.g., when performing an eye test other than visual acuity, not involving distance vision). In some cases, the occluder may occlude the untested eye and, for the tested eye, the occluder may block one spectrum (e.g., visible light) but let another spectrum (e.g., near-infrared (IR) light) through. In some cases the occluder may include a series of illuminators (e.g., visible and/or near-IR) that are configured towards the user and can be turned on and off (e.g., to perform measurements of the eye, such as for pupillometry). The tablet or computer would then measure the pupil size in response to the different illumination conditions. The QR code can identify the type of test (e.g., near vision) being performed, the presence/absence of a lens (e.g., absent in this case), the eye that is being tested (e.g., not occluded), and/or the type of lens when present (e.g., a power level). In some cases, the visual indicator may comprise other symbols, such as letters, geometrical shapes, text, images, and/or colors.

Several aspects of the disclosure with reference to the appended drawings are now explained. Whenever the shapes, relative positions and other aspects of the parts described are not explicitly defined, the scope of the invention is not limited only to the parts shown, which are meant merely for the purpose of illustration. Also, while numerous details are set forth, it is understood that some aspects of the disclosure may be practiced without these details. In other instances, well-known circuits, structures, and techniques have not been shown in detail so as not to obscure the understanding of this description.

FIG. 1 is a block diagram of an example of system 100 for detecting a visual indicator of an occluder for an eye examination. The system 100 may include a device 102 and an occluder 104 with a visual indicator 106. The device 102 could be a handheld computer running a program or application, such as a smartphone or tablet computer. For example, the display screen 110 of the device 102 may be relatively close to the user's eyes and face, e.g., within an arm's length. The device 102 may include a camera 108 (e.g., a front facing built-in camera oriented in a first direction), a display screen 110 (e.g., a front facing built-in touchscreen oriented in the first direction), an input interface 112 (e.g., the touchscreen or a microphone), and a controller 114 (e.g., a processor configured to execute instructions stored in a memory). With additional reference to FIG. 2, the user can utilize the device 102 to self-administer an eye examination, such as a visual acuity test, astigmatism test, or color test displayed via the display screen 110. The eye examination may require that one of the user's eyes remains open while the other of the user's eyes is closed. In some cases, the user may hold the occluder 104 against the user's face while holding or resting the device 102 within an arm's length when performing the eye examination.

Figure 3:
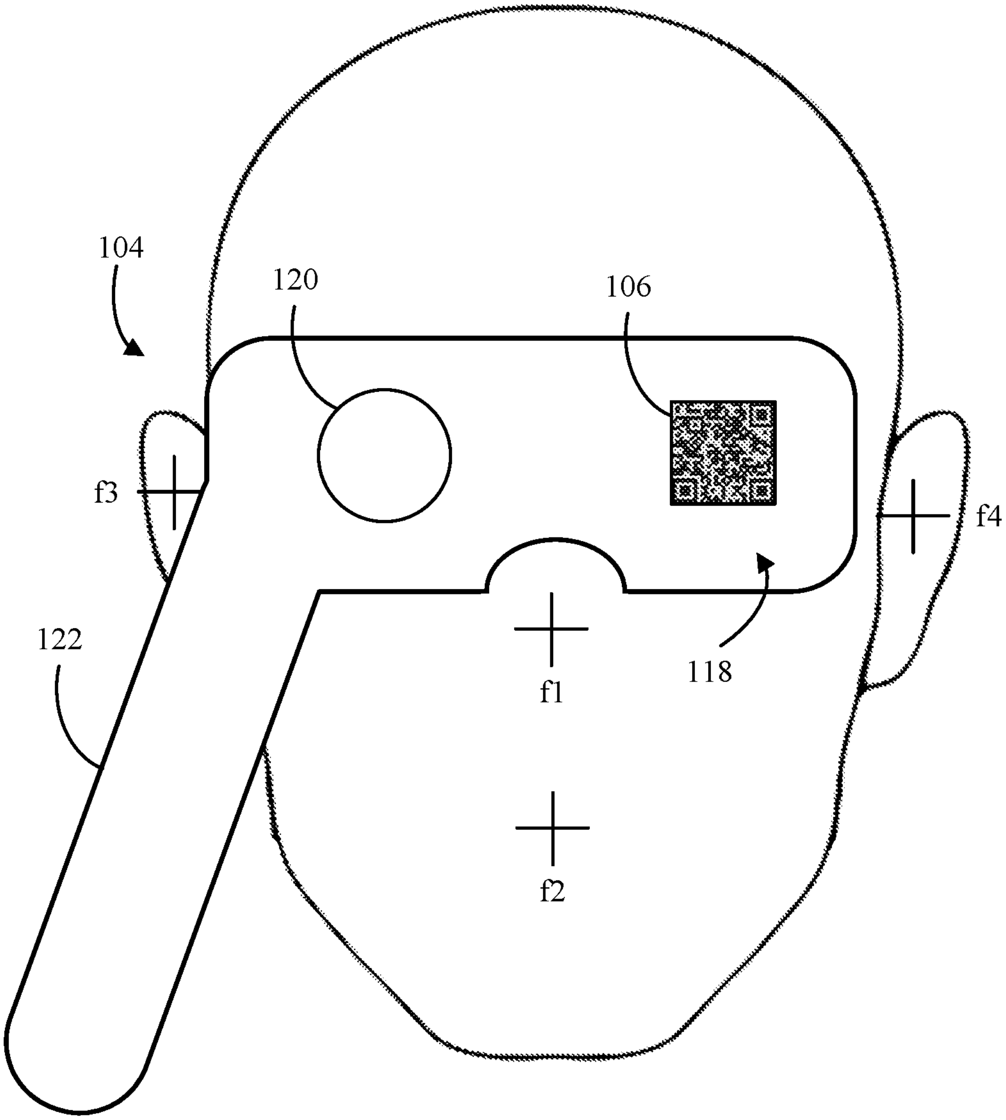
FIG. 3 is an example of an occluder including a visual indicator.

With additional reference to FIG. 3, the occluder 104 can include the visual indicator 106 to improve performance of the eye examination. In some cases, the user may obtain the occluder 104, with the visual indicator 106, for example via parcel post or mail sent to them upon registration of the device 102 via the application. The visual indicator 106 could be a QR code, barcode, or other visual symbol, such as one or more letters, geometrical shapes, text, images, or colors. For example, the visual indicator 106 may have been printed or formed on an adhesive label that is attached to an appropriate location on the body of the occluder 104. In some implementations, the visual indicator 106 may be attached to the occluder 104 in a position corresponding to an eye that is being occluded. For example, the occluder 104 could be manufactured to block at least a portion of light to one eye with the visual indicator 106 arranged in an area of the occluder 104 corresponding to the one eye. The visual indicator 106 may encode information about the occluder 104 as described herein.

Figure 2:
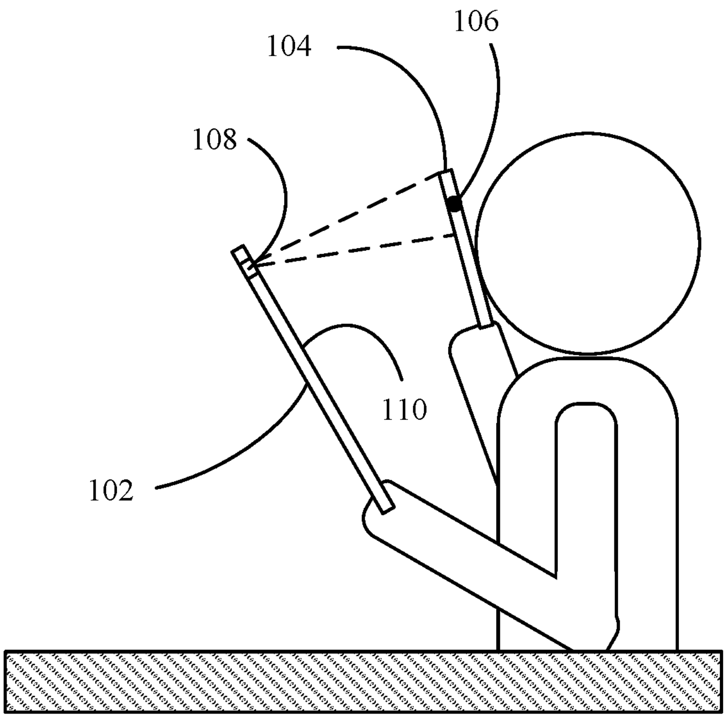
FIG. 2 is an example of administering an eye examination to a user.

The occluder 104 may include an opaque surface 118 that blocks all light (e.g., a complete occluder) or a portion of light (e.g., a pinhole occluder) to one of the user's eyes. For example, as shown in FIG. 2, the left eye of the user is occluded by the opaque surface 118. The occluder 104 can help the user to ensure that the correct eye is properly closed (e.g., the untested eye, such as the left eye, via the opaque surface 118) when performing the eye examination via the device 102. In some implementations, the occluder 104 may include a lens 120 (e.g., an optical lens) to simulate distance vision for the user. For example, the lens can simulate a greater distance (e.g., 20 feet) than exists between the user and the display screen 110 (e.g., the arm's length, such as 1-3 feet). The lens 120, when present, can be placed to cover the other of the user's eyes (e.g., the tested eye, such as the right eye) to simulate distance vision between the user and the display screen 110 of the device 102. In some implementations, the lens 120 can be configured in the occluder 104 with different powers to simulate different distances between the user's face and the display screen 110. For example, the different powers of lenses may be used for different eye tests and/or utilization of different devices (e.g., desktops, laptops, smartphones, or tablet computers), which might require a different eye to device distance to account for their different screen resolutions and/or input devices (touch screen vs. voice, for example). The lens 120 can simulate a correct distance, based on the device 102, when performing the eye examination. In some implementations, the occluder 104 may include a handle 122 to enable the user to hold the occluder 104 against the user's face with one hand while the user is also holding the device 102 (e.g., a smartphone or tablet) in another hand at an arm's length or while the device 102 rests in a support stand. In some implementations, the occluder 104 may be configured as eyewear that include frames to rest on the user's face and arms to rest on the user's cars. For example, the occluder 104 could be configured like a pair of eyeglasses. Instead of the handle 122, the occluder 104 could have left and right arms that rest on the user's left and right cars, respectively. The occluder 104 could also have a bridge that rests on the user's nose. Additionally, where lenses normally appear in eyeglasses, the occluder 104, configured as eyewear, could include the opaque surface 118, with the visual indicator 106, over one eye, and the lens 120, a transparent surface (e.g., plastic), or open air over the other eye. As a result, in some cases, a user could utilize the occluder 104 (e.g., configured as eyewear) and the device 102 (e.g., resting in a support stand) hands-free.

In some implementations, the user can flip the occluder 104 to utilize an opposite side (e.g., a mirror image of the occluder) for the same eye examination or a different eye examination. For example, flipping the occluder 104 may enable covering the right eye with the opaque surface 118 instead of the left eye, covering the left eye with the lens 120 instead of the right eye, and exposing a second visual indicator located on the opposite side (e.g., encoding some information that may be different from the visual indicator 106, such as to indicate the opposite side). In some cases, the user can use the same occluder (e.g., the occluder 104) for multiple eye examinations administered by the device 102. For example, the user can use the occluder 104 for a first eye examination for visual acuity, followed by a second eye examination for astigmatism, then a third eye examination for color blindness. In some cases, the user can use multiple occluders in succession for one or more eye examinations administered by the device 102. For example, the user can use the occluder 104 for a first eye examination for visual acuity, followed by a second occluder having a second visual indicator (e.g., encoding information that may be different from the visual indicator 106) for a second eye examination for astigmatism of color blindness.

In operation, the device 102 may detect, via the camera 108 and the controller 114, the occluder 104 while the occluder is covering at least a portion of the user's face. The device 102 may also detect, via the camera 108 and the controller 114, the visual indicator 106 located on the occluder 104. In some implementations, the device 102 can utilize object detection, object classification, and/or computer vision to detect one or more anatomic features of the user's face, such as the user's nose (f1), mouth (f2), left ear (f3), right ear (f4), left eye, and/or right eye. The device 102 can utilize the object detection, object classification, and/or computer vision to detect the occluder 104 covering the user's face, in a correct position, relative to the one or more anatomic features (e.g., above f1 and f2, and between f3 and f4, and covering the left eye and/or the right eye). For example, the device 102 can determine the eye of the user covered by the opaque surface 118 (e.g., the left eye) and/or the eye of the user covered by the lens 120 (e.g., the right eye). The device 102 can also utilize the object detection, object classification, and/or computer vision to detect the visual indicator 106 located on the occluder 104. The device 102 can detect the visual indicator 106 is on a surface that is opposite of another surface that is against the user's face (e.g., in the correct position).

The device 102, via the controller 114, can then decode information encoded by the visual indicator 106. For example, the device 102 can utilize the camera 108 to scan the QR code or barcode and/or to recognize the letters, geometrical shapes, text, images, or colors. In some implementations, the controller 114 may access a data structure 124 to decode the information from the visual indicator 106. For example, the data structure 124 may comprise a look up table that correlates an identification number given by the visual indicator 106 to the information being decoded. In some cases, the data structure 124 may be stored locally by the device 102. In other cases, the device 102 may access the data structure 124 via a wireless connection to a remote server.

The information encoded by the visual indicator 106 may indicate description of the occluder 104, such as a unique identification number, a type of occluder (e.g., a complete occluder or a pinhole occluder), an eye covered by the opaque surface 118, a presence or absence of a lens (e.g., the lens 120), the eye that is being tested (e.g., not occluded), a power of the lens when present (e.g., used to simulate distance vision), an eye covered by the lens when present, types of tests that may be performed with the occluder (e.g., visual acuity, astigmatism, or color blindness), and/or information about the user to whom the occluder 104 has been assigned. The device 102 can configure a GUI to display, at the display screen 110, an eye examination administered to the user (e.g., an eye test). In some implementations, the eye examination may be determined based on the information decoded from the visual indicator 106. In some implementations, the eye examination may be accessed from the data structure 124.

The device 102 can then administer the eye examination to the user, including by obtaining test input from the user, via the input interface 112, during the administration of the eye examination. For example, the device 102 can administer a visual acuity test by displaying a Snellen chart, to the display screen 110, at a predetermined size and resolution. The device 102 can then receive the test input from the user, via the input interface 112, indicating a lowest line that the user can read on the Snellen chart. The device 102 can then output, via the device 102, a result of the eye examination. The result may be determined based on the test input from the user (e.g., the lowest line) and the information encoded by the visual indicator 106 (e.g., the power of the lens). In some implementations, the device 102 may output the result of the eye examination as a confirmation (e.g., pass or fail) or score (e.g., percentage), including to the display screen 110 or to speakers or headphones of the device 102. As a result, the system 100 may enable the eye examination to be administered while reducing inconvenience to the user, errors in the eye examination, and/or delays in the performance of the eye examination.

In some implementations, the device 102 may determine (e.g., via the controller 114 and the camera 108, or in some cases, Lidar) a distance between the display screen 110 and a user of the device 102. For example, the controller 114 may determine the distance based on a predetermined size of the occluder 104 in an image from the camera 108. The controller 114 may then verify the distance between the display screen 110 and the user is a correct distance for the eye examination to be performed and/or the type of occluder being used before administering the examination. For example, the device 102 may detect that the user is at a required distance, and that the user has covered their eye with the occluder 104 (e.g., the left eye). The device 102 may identify the type of occluder the user is using via the visual indicator 106 encoding the description of the occluder 104. For example, the description may include a power of the lens fitted on occluder, and/or the type of occluder (e.g. utilized for distance vision simulation, or another eye test). The device 102 may automatically recognize the details of the occluder 104 (e.g., the information) without the user entering the information manually, thereby removing potential errors.

In some implementations, the occluder 104 may comprise a simple structure, such as a piece of paper, cardboard, or plastic, with the visual indicator 106 (e.g., the QR code or other visual symbol) located on the structure. For example, the occluder might not include the lens 120 (e.g., when performing an eye test other than visual acuity, and not simulating distance vision). The visual indicator 106 can identify the type of test (e.g., near vision) being performed, the presence/absence of the lens 120 (e.g., absent in this case), the eye that is being tested (e.g., not occluded), and/or the type of lens when present (e.g., a power level).

Figure 4:
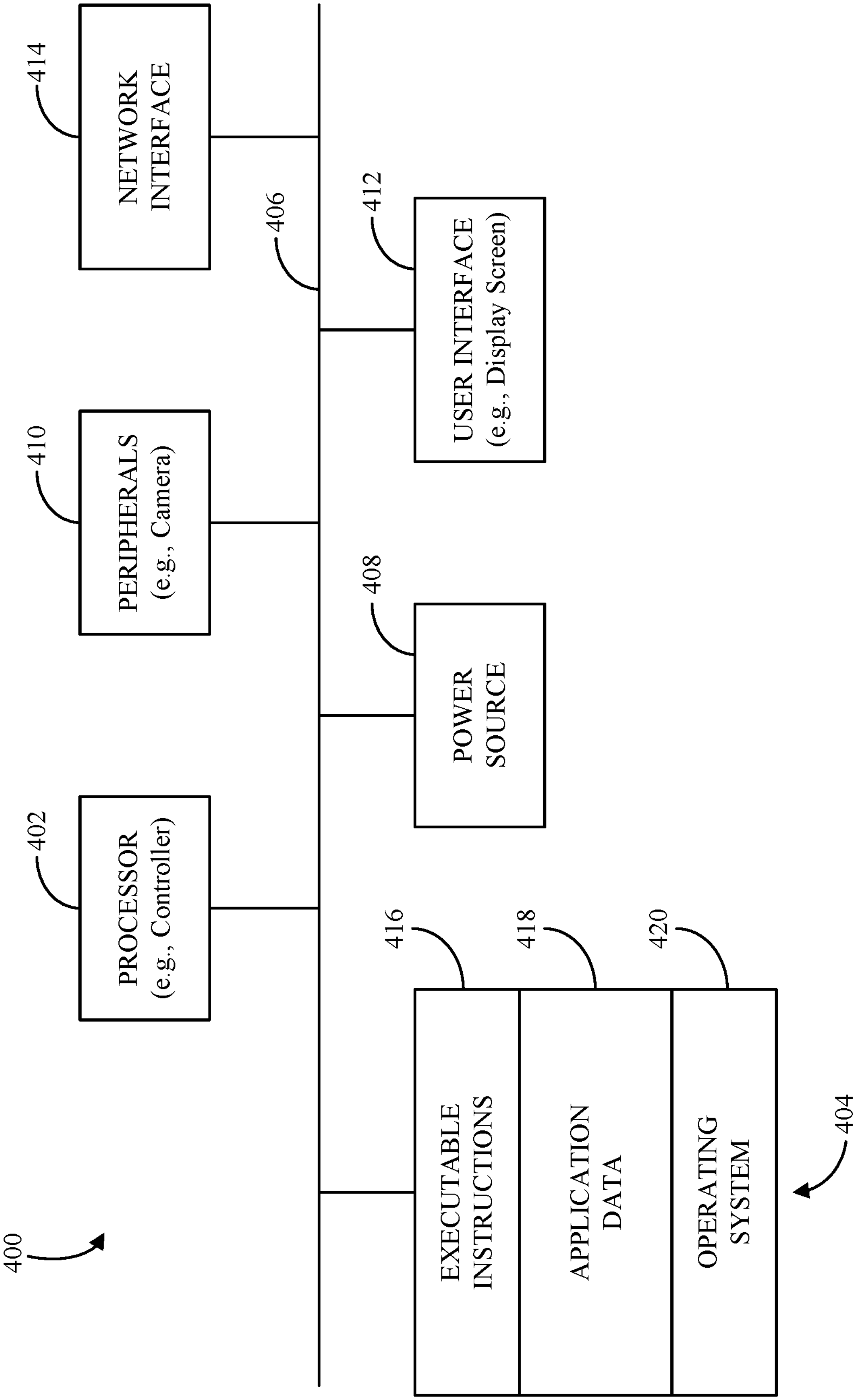
FIG. 4 is a block diagram of an example internal configuration of a computing device for detecting a visual indicator of an occluder for an eye examination.

FIG. 4 is a block diagram of an example internal configuration of a computing device for detecting a visual indicator of an occluder for an eye examination. In one configuration, the computing device 400 may comprise the device 102 for detecting the visual indicator 106 of the occluder 104.

The computing device 400 includes components or units, such as a processor 402, a memory 404, a bus 406, a power source 408, peripherals 410, a user interface 412, a network interface 414, other suitable components, or a combination thereof. One or more of the memory 404, the power source 408, the peripherals 410, the user interface 412, or the network interface 414 can communicate with the processor 402 via the bus 406.

The processor 402 (e.g., the controller 114) is a central processing unit, such as a microprocessor, and can include single or multiple processors having single or multiple processing cores. Alternatively, the processor 402 can include another type of device, or multiple devices, configured for manipulating or processing information. For example, the processor 402 can include multiple processors interconnected in one or more manners, including hardwired or networked. The operations of the processor 402 can be distributed across multiple devices or units that can be coupled directly or across a local area or other suitable type of network. The processor 402 can include a cache, or cache memory, for local storage of operating data or instructions.

The memory 404 includes one or more memory components, which may each be volatile memory or non-volatile memory. For example, the volatile memory can be random access memory (RAM) (e.g., a DRAM module, such as DDR DRAM). In another example, the non-volatile memory of the memory 404 can be a disk drive, a solid state drive, flash memory, or phase-change memory. In some implementations, the memory 404 can be distributed across multiple devices. For example, the memory 404 can include network-based memory or memory in multiple clients or servers performing the operations of those multiple devices.

The memory 404 can include data for immediate access by the processor 402. For example, the memory 404 can include executable instructions 416, application data 418, and an operating system 420. The executable instructions 416 can include one or more application programs, which can be loaded or copied, in whole or in part, from non-volatile memory to volatile memory to be executed by the processor 402. For example, the executable instructions 416 can include instructions for performing some or all of the techniques of this disclosure. The application data 418 can include user data, database data (e.g., database catalogs or dictionaries), or the like. In some implementations, the application data 418 can include functional programs, such as a web browser, a web server, a database server, another program, or a combination thereof. The operating system 420 can be, for example, Microsoft Windows®, Mac OS X®, or Linux®; an operating system for a mobile device, such as a smartphone or tablet device; or an operating system for a non-mobile device, such as a mainframe computer.

The power source 408 provides power to the computing device 400. For example, the power source 408 can be an interface to an external power distribution system. In another example, the power source 408 can be a battery, such as where the computing device 400 is a mobile device or is otherwise configured to operate independently of an external power distribution system. In some implementations, the computing device 400 may include or otherwise use multiple power sources. In some such implementations, the power source 408 can be a backup battery.

The peripherals 410 (e.g., the camera 108) includes one or more sensors, detectors, or other devices configured for monitoring the computing device 400 or the environment around the computing device 400. For example, the peripherals 410 can include a front facing built-in camera. In another example, the peripherals can include a plurality of camera for testing vision of the user. In another example, the peripherals can include a range detection system, such as Lidar, for determining a distance to the user. In another example, the peripherals can include a geolocation component, such as a global positioning system location unit.

The user interface 412 includes one or more input interfaces and/or output interfaces. An input interface (e.g., the input interface 112) may, for example, be a positional input device, such as a mouse, touchpad, touchscreen, or the like; a keyboard; or another suitable human or machine interface device. An output interface (e.g., the display screen 110) may, for example, be a display, such as a liquid crystal display, a cathode-ray tube, a light emitting diode display, virtual reality display, or other suitable display. In another example, the output interface may include speakers or headphones.

The network interface 414 provides a connection or link to a network. The network interface 414 can be a wired network interface or a wireless network interface. The computing device 400 can communicate with other devices via the network interface 414 using one or more network protocols, such as using Ethernet, transmission control protocol (TCP), internet protocol (IP), power line communication, an IEEE 802.X protocol (e.g., Wi-Fi, Bluetooth, or ZigBee), infrared, visible light, general packet radio service (GPRS), global system for mobile communications (GSM), code-division multiple access (CDMA), Z-Wave, another protocol, or a combination thereof. In some cases, the network interface 414 may enable communication with the data structure 124.

Figure 5:
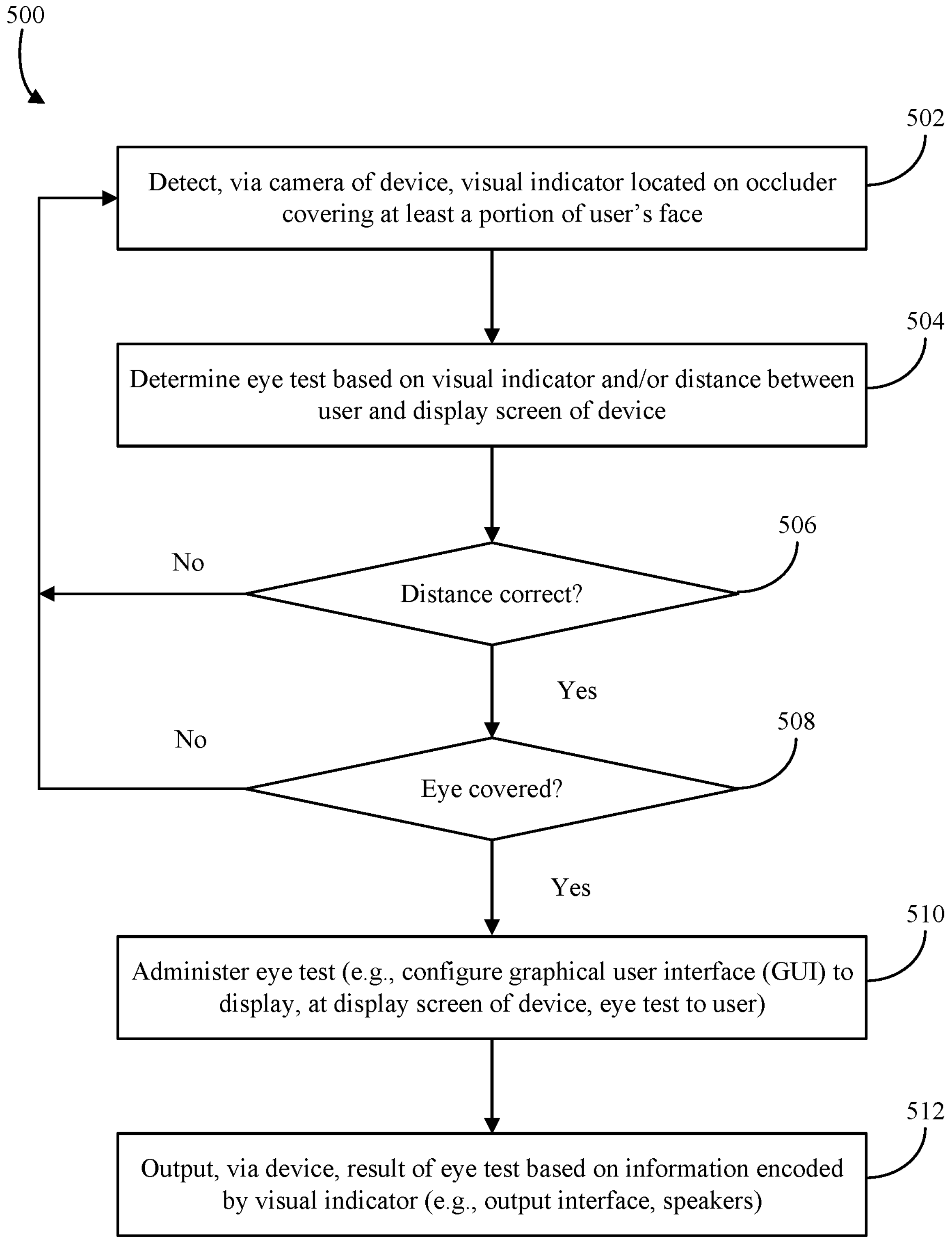
FIG. 5 is a flowchart of an example of a process for detecting a visual indicator of an occluder for an eye examination.

FIG. 5 is a flowchart of an example of a process 500 for detecting a visual indicator of an occluder for an eye examination. The process 500 can be executed using computing devices, such as the systems, hardware, and software described with respect to FIGS. 1-4. The process 500 can be performed, for example, by executing a machine-readable program or other computer-executable instructions, such as routines, instructions, programs, or other code. The operations of the process 500 or another technique, method, process, or algorithm described in connection with the implementations disclosed herein can be implemented directly in hardware, firmware, software executed by hardware, circuitry, or a combination thereof.

For simplicity of explanation, the process 500 is depicted and described herein as a series of operations. However, the operations in accordance with this disclosure can occur in various orders and/or concurrently. Additionally, other operations not presented and described herein may be used. Furthermore, not all illustrated operations may be required to implement a technique in accordance with the disclosed subject matter.

At operation 502, a device may detect, via a camera of the device, a visual indicator located on an occluder while the occluder is covering at least a portion of a user's face. For example, the device 102, running an application, may detect, via the camera 108, the visual indicator 106 located on the occluder 104 while the occluder is covering at least a portion of a user's face. In another example, the device 102 can utilize object detection, object classification, and/or computer vision to detect the user, to detect the occluder, to detect the position of the occluder relative to the user, and/or to detect the visual indicator located on the occluder.

At operation 504, the device may determine an eye test to be performed based on visual indicator that is detected. For example, the device 102 may determine a visual acuity test should be performed based on the visual indicator 106. The device may also determine a distance between the user and the display screen of the device (e.g., the display screen 110). For example, the device may determine the distance based on a predetermined size of the occluder in an image from the camera.

At operation 506, the device may determine whether the user is a correct distance from the display screen based on the eye test to be performed and/or the occluder being used. If the user is not at a correct distance from the display screen (e.g., "No," such as the user being too close to the display screen or too far from the display screen), the process may return to operation 502 (e.g., waiting for a different occluder, or a change in distance). However, if the user is at a correct distance from the display screen (e.g., "Yes," such as the user being within a predetermined range, which could include an arm's length), the process may continue to operation 508.

At operation 508, the device may determine whether the user's eye is properly covered for the test. This may include the occluder in the correct position with an opaque surface covering the correct eye (e.g., the left eye) and/or a lens over the other eye (e.g., the right eye). If the user's eye is not properly covered (e.g., "No," such as the occluder being out of position), the process may return to operation 502 (e.g., waiting for the occluder to be put into the correct position). However, if the user's eye is properly covered (e.g., "Yes"), the process may continue to operation 510.

At operation 510, the device may configure a GUI to display, at the display screen of the device, an eye examination administered to the user. For example, the device 102 may configure the GUI to display a visual acuity test (e.g., a Snellen chart) to the display screen 110. In some implementations, the device may determine the eye examination to administer based on a decoding of the visual indicator.

At operation 512, the device may output, via the display screen, speakers, or headphones, a result of the eye examination. The result may be based on information encoded by the visual indicator (e.g., indicating the eye examination being administered, and the power of lens being used) and/or test input from the user (e.g., indicating a lowest line the user can read on the Snellen chart). In some implementations, the device may output the result of the eye examination as a confirmation (e.g., pass or fail) or score (e.g., percentage).

Some implementations may include a method for eye examination, comprising detecting, via a camera of a device, a visual indicator located on an occluder while the occluder is covering at least a portion of a user's face; configuring a GUI to display, at a display screen of the device, an eye examination administered to the user; and outputting, via the device, a result of the eye examination based on information encoded by the visual indicator. In some implementations, the detecting includes detecting a lens of the occluder covering an eye of the user. In some implementations, the information indicates a power of the lens used to simulate distance vision. In some implementations, the detecting includes detecting an opaque surface of the occluder covering an eye of the user. In some implementations, a type of the occluder is identified by the information. In some implementations, the information indicates the eye examination, from a plurality of eye examinations, to be performed. In some implementations, the eye examination is a test for visual acuity. In some implementations, the occluder is configured as eyewear that include frames to rest on the user's face and arms to rest on the user's cars. In some implementations, the visual indicator is a QR code that indicates a power of a lens and an identification of an occluder. In some implementations, the method may include determining, via the camera, a distance between the user and the display screen; and verifying the distance before administering the eye examination. In some implementations, the occluder includes a handle to be held in one hand of the user to hold the occluder against the user's face, and the device is a portable electronic device to be held in another hand of the user at an arm's length.

Some implementations may include device, such as a handheld computing device, comprising a front facing built-in camera oriented in a first direction; a display screen oriented in the first direction; a memory; and a processor configured to execute instructions stored in the memory to determine a distance between the display screen and a user of the handheld computing device; determine, via the front facing built-in camera, an eye of the user covered by an occluder; detect, via the front facing built-in camera, a visual indicator located on the occluder while the occluder is covering at least a portion of a user's face; configure a GUI to display, via the display screen, an eye examination to the user; and output, via the display screen, a result of the eye examination based on information encoded by the visual indicator. In some implementations, the handheld computing device is a smartphone or a tablet computer. In some implementations, determining whether the eye of the user is covered by the occluder includes determining whether the eye is a left eye of the user or a right eye of the user. In some implementations, the detecting includes detecting the visual indicator on a surface that is opposite of another surface that is against the user's face. In some implementations, the detecting includes detecting a lens of the occluder covering another eye of the user. In some implementations, the information indicates the eye examination, from a plurality of eye examinations, to be performed.

Some implementations may include a non-transitory computer readable medium storing instructions operable to cause one or more processors to perform operations comprising detecting, via a camera of a device of a user, a visual indicator located on an occluder while the occluder is covering at least a portion of a user's face; configuring a GUI to display, at a display screen of the device, an eye examination administered to the user; and outputting, via the device, a result of the eye examination based on information encoded by the visual indicator. In some implementations, the detecting includes detecting a lens of the occluder covering an eye of the user. In some implementations, the information indicates a power of the lens used to simulate distance vision. In some implementations, the detecting includes detecting an opaque surface of the occluder covering an eye of the user. In some implementations, the information indicates the eye examination, from a plurality of eye examinations, to be performed.

In utilizing the various aspects of the embodiments, it would become apparent to one skilled in the art that combinations or variations of the above embodiments are possible for detecting a visual indicator of an occluder for an eye examination. Although the embodiments have been described in language specific to structural features and/or methodological acts, it is to be understood that the appended claims are not necessarily limited to the specific features or acts described. The specific features and acts disclosed are instead to be understood as embodiments of the claims useful for illustration.

What is claimed is:

1. A method for eye examination, comprising:

detecting, via a camera of a device, a visual indicator located on an occluder while the occluder is covering at least a portion of a user's face;

displaying on a display screen of the device a graphical user interface (GUI);

administering an eye examination to the user with the GUI; and outputting, via the device, a result of the eye examination based on information encoded by the visual indicator, wherein the information encoded by the visual indicator includes an occluder characteristic that describes the occluder itself, the occluder characteristic including at least one of: a type of the occluder, an identification of the occluder, an indication of which eye is covered by the occluder, a presence or absence of a lens in the occluder, a power of the lens, or a type of eye examination associated with the occluder, and wherein the result of the eye examination is determined based on both the occluder characteristic and test input from the user.

2. The method of claim 1, wherein the detecting includes detecting a lens of the occluder covering an eye of the user.

3. The method of claim 2, wherein the information indicates a power of the lens used to simulate distance vision.

4. The method of claim 1, wherein the detecting includes detecting an opaque surface of the occluder covering an eye of the user.

5. The method of claim 1, wherein the information indicates the eye examination, from a plurality of eye examinations, to be performed.

6. The method of claim 1, wherein the occluder is configured as eyewear that includes frames to rest on the user's face and arms to rest on the user's ears.

7. The method of claim 1, wherein the visual indicator is a quick response (QR) code that indicates a power of a lens and an identification of an occluder.

8. The method of claim 1, further comprising:

determining, via the camera, a distance between the user and the display screen; and verifying the distance before administering the eye examination.

9. The method of claim 1, wherein the occluder includes a handle to be held in one hand of the user to hold the occluder against the user's face, and the device is a portable electronic device to be held in another hand of the user.

10. A handheld computing device, comprising:

a front facing built-in camera oriented in a first direction;

a display screen oriented in the first direction; and a processor coupled to memory storing instructions that, when executed by the processor cause the handheld computing device to perform operations including:

determine a distance between the display screen and a user of the handheld computing device;

determine, via the front facing built-in camera, an eye of the user covered by an occluder;

detect, via the front facing built-in camera, a visual indicator located on the occluder while the occluder is covering at least a portion of a user's face;

display, on a display screen of the device, a graphical user interface (GUI);

administer an eye examination to the user with the GUI; and output, via the display screen, a result of the eye examination based on information encoded by the visual indicator, wherein the information encoded by the visual indicator includes an occluder characteristic that describes the occluder itself and wherein the result of the eye examination is determined based on both the occluder characteristic and test input from the user.

11. The handheld computing device of claim 10, wherein the handheld computing device is a smartphone or a tablet computer.

12. The handheld computing device of claim 10, wherein determining the eye of the user covered by the occluder includes determining whether the eye is a left eye of the user or a right eye of the user.

13. The handheld computing device of claim 10, wherein the detection includes detecting the visual indicator on a surface that is opposite of another surface that is against the user's face.

14. The handheld computing device of claim 10, wherein the detection includes detecting a lens of the occluder covering another eye of the user.

15. The handheld computing device of claim 10, wherein the information indicates the eye examination, from a plurality of eye examinations, to be performed.

16. A non-transitory computer readable medium storing instructions operable to cause one or more processors to perform operations comprising:

detecting, via a camera of a device of a user, a visual indicator located on an occluder while the occluder is covering at least a portion of a user's face;

displaying on a display screen of the device a graphical user interface (GUI);

administering an eye examination to the user with the GUI; and outputting, via the device, a result of the eye examination based on information encoded by the visual indicator, wherein the information encoded by the visual indicator includes an occluder characteristic that describes the occluder itself and wherein the result of the eye examination is determined based on both the occluder characteristic and test input from the user.

17. The non-transitory computer readable medium storing instructions of claim 16, wherein the detecting includes detecting a lens of the occluder covering an eye of the user.

18. The non-transitory computer readable medium storing instructions of claim 17, wherein the information indicates a power of the lens used to simulate distance vision.

19. The non-transitory computer readable medium storing instructions of claim 16, wherein the detecting includes detecting an opaque surface of the occluder covering an eye of the user.

20. The method of claim 1, further comprising:

configuring the eye examination based on the information.

21. The method of claim 20, wherein configuring the eye examination based on the information comprises determining a size or a resolution of the GUI based on the information.

* * * * *